(12) United States Patent
Laufer et al.

(10) Patent No.: US 8,628,526 B2
(45) Date of Patent: Jan. 14, 2014

(54) DEVICES AND METHODS FOR TISSUE APPOSITION

(76) Inventors: Michael D. Laufer, Menlo Park, CA (US); Jeremy S. Laufer, Menlo Park, CA (US)

(*) Notice: Subject to any disclaimer, the term of this patent is extended or adjusted under 35 U.S.C. 154(b) by 0 days.

(21) Appl. No.: 13/224,513

(22) Filed: Sep. 2, 2011

(65) Prior Publication Data

US 2012/0143187 A1    Jun. 7, 2012

Related U.S. Application Data

(63) Continuation of application No. 11/313,191, filed on Dec. 19, 2005, now Pat. No. 8,012,151.

(60) Provisional application No. 60/637,203, filed on Dec. 17, 2004.

(51) Int. Cl.
  *A61B 18/18* (2006.01)
(52) U.S. Cl.
  USPC ............................................................ 606/41
(58) Field of Classification Search
  USPC .......................................... 606/41; 128/898
  See application file for complete search history.

(56) References Cited

U.S. PATENT DOCUMENTS

| | | |
|---|---|---|
| 6,083,255 A | 7/2000 | Laufer et al. |
| 6,200,333 B1 | 3/2001 | Laufer |
| 6,267,751 B1 | 7/2001 | Mangosong |
| 7,186,251 B2 | 3/2007 | Malecki et al. |
| 2005/0101984 A1 | 5/2005 | Chanduszko et al. |
| 2005/0143763 A1 | 6/2005 | Ortiz et al. |
| 2005/0251201 A1 | 11/2005 | Roue et al. |
| 2007/0112347 A1 | 5/2007 | Malecki et al. |

FOREIGN PATENT DOCUMENTS

WO    WO 2004/086944    10/2004

OTHER PUBLICATIONS

U.S. Appl. No. 11/313,191, filed Dec. 19, 2005 in the name of Laufer, final Office Action dated Feb. 24, 2010.
U.S. Appl. No. 11/313,191, filed Dec. 19, 2005 in the name of Laufer, non-final Office Action dated Sep. 7, 2010.
U.S. Appl. No. 11/313,191, filed Dec. 19, 2005 in the name of Laufer, Notice of Allowance dated May 12, 2011.

*Primary Examiner* — Bill Thomson
*Assistant Examiner* — Jeffrey Lipitz
(74) *Attorney, Agent, or Firm* — Levine Bagade Han LLP

(57) ABSTRACT

Devices and methods are described for sealing tissue such as melding the two flaps of the foramen ovale together without the need for a permanent implant or closing openings in vessels.

6 Claims, 8 Drawing Sheets

DEVICES AND METHODS FOR TISSUE APPOSITION

CROSS-REFERENCE TO RELATED APPLICATIONS

This application is a continuation of U.S. patent application Ser. No. 11/313,191, filed Dec. 19, 2005 which claims the benefit of U.S. Provisional Application No. 60/637,203 filed Dec. 17, 2005, the contents of which are incorporated by reference in their entirety.

BACKGROUND OF THE INVENTION

Traditional tissue closure devices such as staples, sutures, adhesives, etc. while useful, may not be best suited for every indication. For example, a tissue closure system that eliminates the need for any implant (such as an anchor, suture, clip, etc.) may be well suited for minimally invasive tissue closure and/or may decrease patient recovery time. The term tissue closure may comprise sealing, melding, or otherwise fastening together various tissue and/or closing an opening in tissue after the creation of an opening. To accomplish tissue closure, the devices and methods minimally damage the tissue (e.g., by the application of energy) producing a healing response that generates collagen. To assist in tissue closure, the methods and devices may also apply compression to the tissue(s) to be sealed. Heating the tissue causes various factors to be secreted by the tissue, including factors such as tissue necrosis factor beta, tissue plasminogen activator, and others that result in migration of fibrocytes that secrete collagen.

The following two examples of tissue closure illustrate situations highlighting the need for tissue closure devices. However, it is understood that the invention described herein may also have a broad range of applicability beyond the illustrated examples.

One instance requiring tissue closure systems results from incomplete development of a body organ or pathway. Many circumstances occur in nature, and particularly in mammals, involving incomplete development of the embryo and early infant. One such circumstance occurs during the conversion from intrauterine circulation without lungs, to extrauterine circulation dependant on lung gas transfer.

During intrauterine circulation, a fetus does not use it's own lungs to oxygenate the blood. Instead, the mother's placenta supplies the fetus with oxygenated blood through the umbilical cord. Therefore, during intrauterine circulation, it is not necessary for the blood to travel from the fetus' heart to its lungs and then back to its heart. As shown in FIG. 1, a small opening in the atrial septum 2 comprises adjacent flaps of tissue 4 and 6. This opening, the foramen ovale, allows the blood (as shown by arrow A) to skip the fetus' lungs and travel from the veins to the right side 3' of the fetus' heart directly to the left side 3" of the heart. The foramen ovale generally consists of two flaps of the atrial wall. Normally, during the conversion to extrauterine circulation at birth, the foramen ovale closes as a result of blood pressure on the left side of the heart and subsequent healing between the two flaps. This appears to be, in part, dependant on prostaglandins and other tissue factors. The condition where the forum ovate fails to close is called patent forum ovale (PFO).

Natural pathways such as the ductus arteriosus and foramen ovale, normally close after birth. In some circumstances, however, these pathways remain patent or partially open, and the PFO allows improper blood flow or foreign material, such as blood clots, to move into the bodily circulation. This condition may result in strokes, heart attacks, or can change the pressure and volume of blood going to the brain and other organs, perhaps causing migraine headaches. It is beneficial to close these pathways, but conventional procedures involve major surgery to open the chest and heart while the patient requires artificial circulation on a heart-lung bypass machine. Some procedures have attempted placement of artificial appliances/devices through the patent foramen ovale in an attempt to keep both loose flaps from separating without actually melding them together.

Another example requiring tissue closure involves closure of blood vessels. Access to the circulation for procedures such as angioplasty and/or stent placement into the coronary arteries often involve arterial puncture sites. Conventionally, closure of these arterial access sites involves sutures or thrombogenic sponges, or similar foreign objects. However, these solutions require that the patient remain immobile while the natural clotting and healing process occurs at the puncture site.

BRIEF SUMMARY OF THE INVENTION

The invention described herein may be used to seal tissue together. For example, the invention includes devices and methods for permanently melding the two flaps of the foramen ovale together without the need for a permanent implant. Some natural benefits of this approach include elimination of any foreign material, such as suture material, being left behind at the closure site. In the case of vascular closure, the vessel would be closed immediately after the procedure, providing the patient with almost immediate mobility.

DETAILED DESCRIPTION OF THE INVENTION

The device and method described herein allow the trained practitioner to seal tissue without the need for suture or other foreign material to be left behind.

Figure 1:
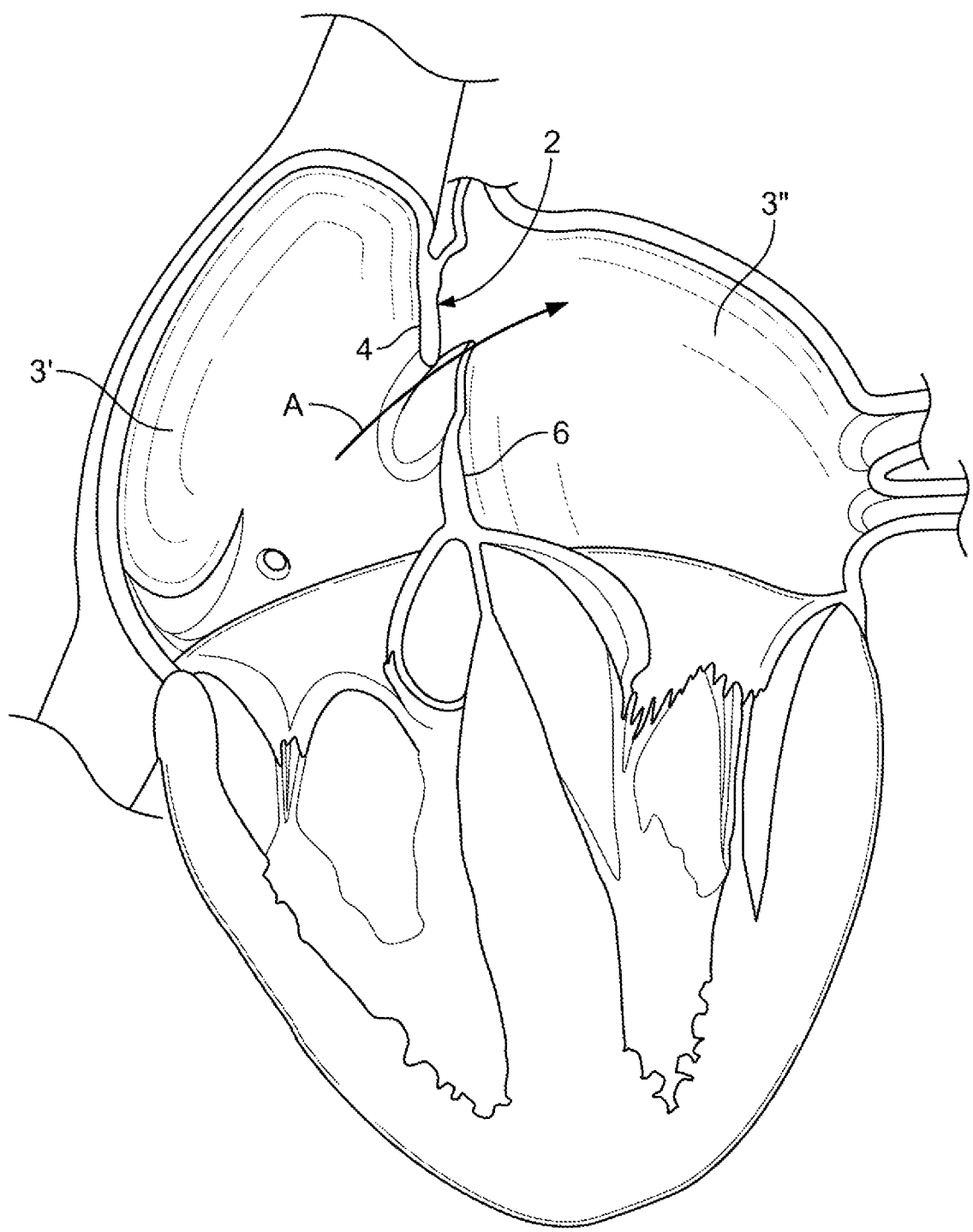
FIG. 1 depicts the anatomic defect of patent foramen ovale.
Figure 2A:
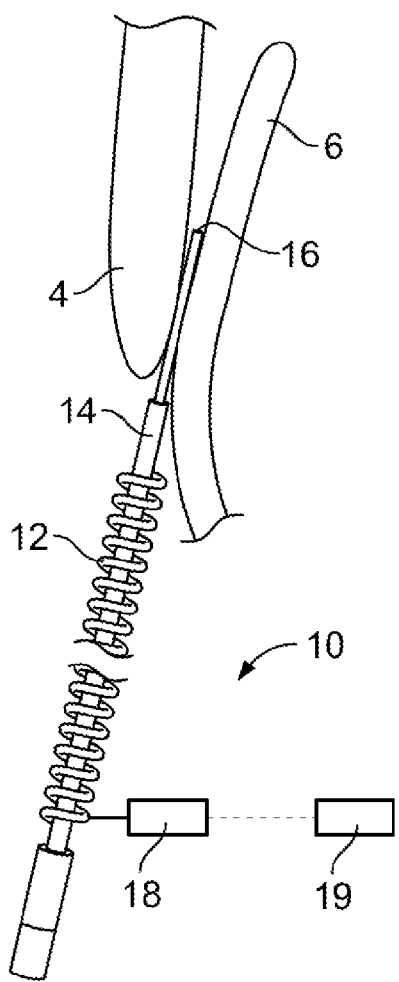
FIGS. 2a-2c depicts a variation closing the patent foramen ovale in accordance with the invention described herein.

As shown in FIG. 2a, a variation of the inventive system 10 includes a helical member 12 and a placement member (e.g., catheter) 14. It is noted that the system 10 may include an advancing mechanism 18 to thread the helical member 12 onto the catheter 14. As such, the helical member 12 may be made to accommodate any number of catheters. Alternatively, the helical member 12 may be provided with a catheter. In addition, the helical member 12 will be coupled in some manner to a power supply 19 to deliver energy for the treatment. The coupling may take place using connections on the catheter or a direct connection between the helical member 12 and the power supply 19.

Figure 2B:
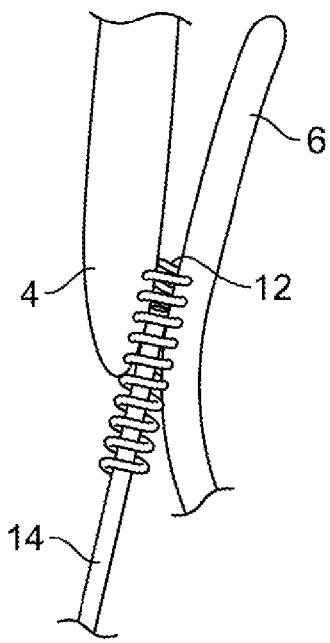

In one example of a method for closure of patent foramen ovale (PFO), the practitioner places a guide wire into a vein, usually in the groin area, and advances the guide wire into the right atrium of the heart. As shown in FIG. 2*a*, the guide wire 16 can then be threaded into the tunnel of the PFO or, alternatively, can be placed alongside a flap of the PFO (e.g., 4 or 6) without entering the tunnel. The placement catheter 14 then advances over the wire into the right atrium. Suction may be optionally applied through the catheter such that the catheter tip is apposed to the atrial wall and more specifically to the right side of the PFO. The helical member 12 then advances over the catheter 12 until it contacts the tip of the catheter 12. As shown in FIG. 2*b*, the helical member 12 is then rotated to engage the tissue of the right and left sides of the PFO. The tip of the helical member 12 may be configured to ease penetration of tissue once it leaves the surface of the catheter 14. Accordingly, the tip of the helical member 12 along with the remainder of the coils may have a low profile when placed on the catheter 14 so that the medical practitioner does not experience undue resistance when advancing the helical member 12 and/or catheter 14 to the treatment site. It is noted that the guide wire may or may not be withdrawn when advancing the helical member 12 into the tissue.

Figure 2C:
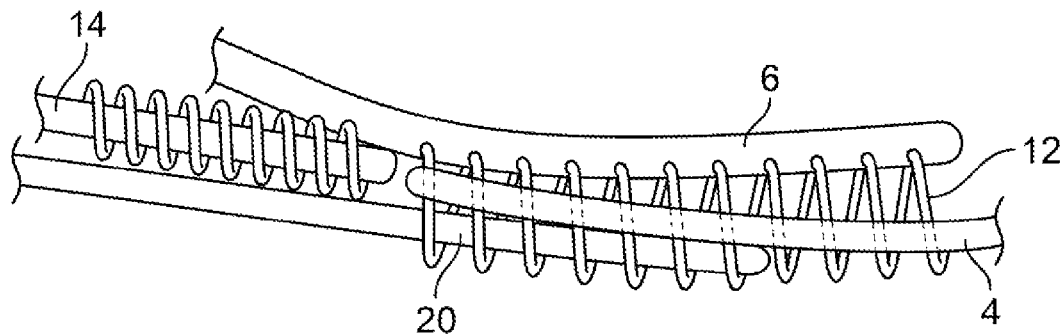

Next, the tissue flaps 4 and 6 are drawn together. This may be accomplished any number of ways. The helical member 12 may draw the tissue together mechanically by reducing in diameter by drawing the coils together. In one example, the helical member 16 may be fabricated from a shape memory alloy (e.g., Nitinol) that compresses the tissue upon energizing and/or heating of the helical member 12. Alternatively, or in combination, as illustrated in FIG. 2*c*, the obturator may be advanced within the coils of the helical member 12. In this case, the helical member 12 is advanced entirely through the flap of tissue 4 so that the obturator may be placed externally to the PFO tunnel causing the helical member 12 to compress the flaps of tissue together. As shown in FIGS. 2*a*-2*c*, the helical member 12 may be inserted into the tissue without passing entirely through the tissue (as shown in FIGS. 2*a* and 2*b*). However, in some cases, the tissue may be too thin, or the medical practitioner may wish to pass the helical member 12 entirely through one or more of the flaps of tissue (as shown in FIG. 2*c*).

It should be noted that a balloon, or other device may be substituted for the obturator 20. All that is required is that the member advanced into the coils of the helical member 12 compress the tissue flaps 4 and 6 together.

Figure 2D:
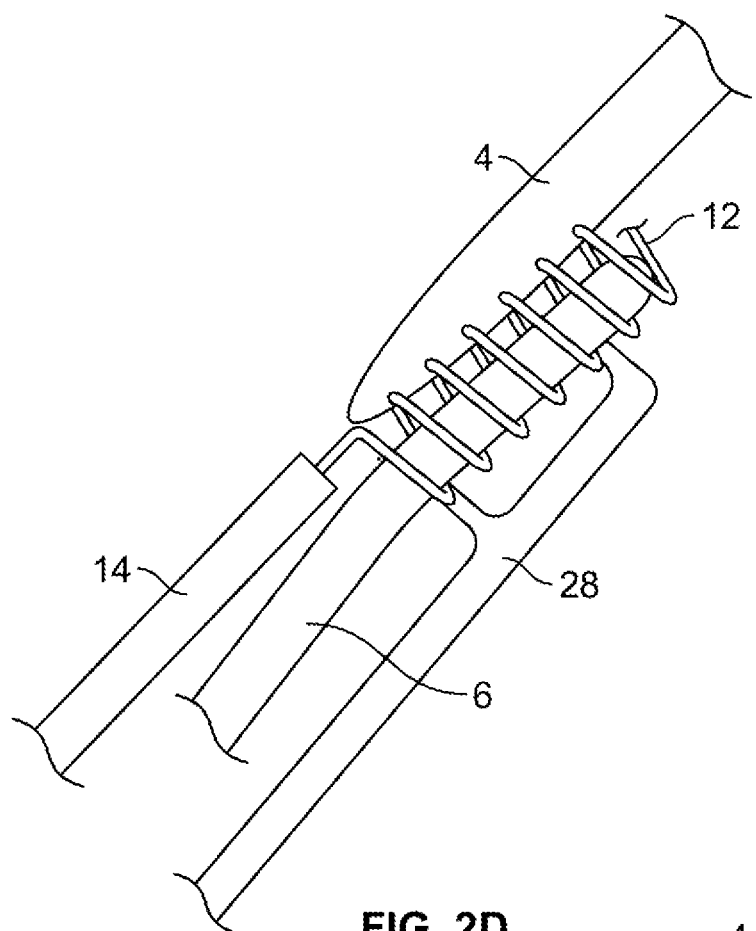
FIGS. 2d-2e illustrate another variation of the inventive system.
Figure 2E:
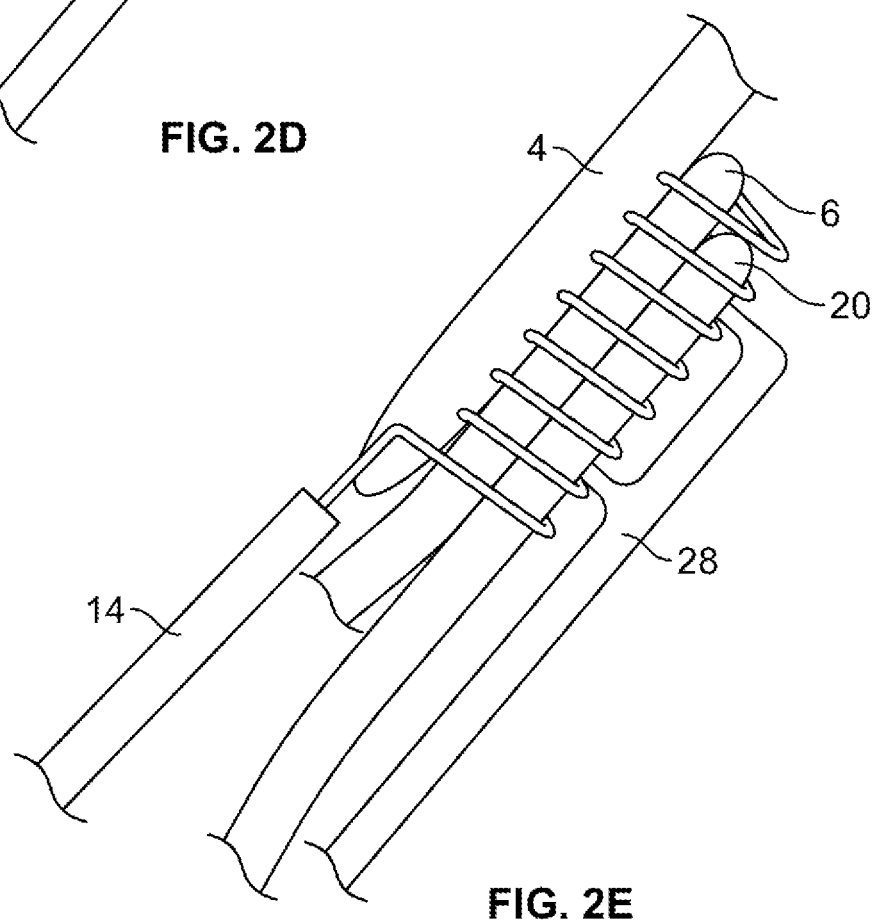

FIGS. 2*d*-2*e* illustrate another variation of the inventive system. As illustrated, a vacuum device 28 may be used to secure the tissue being treated. In this variation, the vacuum device 28 secures to a flap of tissue 6 to prevent the flap 6 from moving. Once the flap 6 is held in place, the helical member 12 may be threaded into the flaps. As illustrated, the helical member 12 will compress the tissue so that the area may be treated.

After drawing the tissue together, the helical member 12 is then activated to heat the tissue while it is being compressed. After a sufficient time, for example, approximately 2 minutes at 70 degrees C., the heating stops. After 30-60 seconds, after the tissue cools, external compression of the tissue is not required, so the obturator may be removed. The helical member 12 may then be removed via twisting in a direction opposite to the placement rotation. The guide wire may then be removed unless observation indicates the need for further intervention. If the medical practitioner desires to confirm closure of the PFO a contrast agent, such as gas-agitated saline, may be injected. If the PFO is larger or requires further treatment or re-treatment, the process may be repeated until the complete closure is demonstrated.

Figure 3:
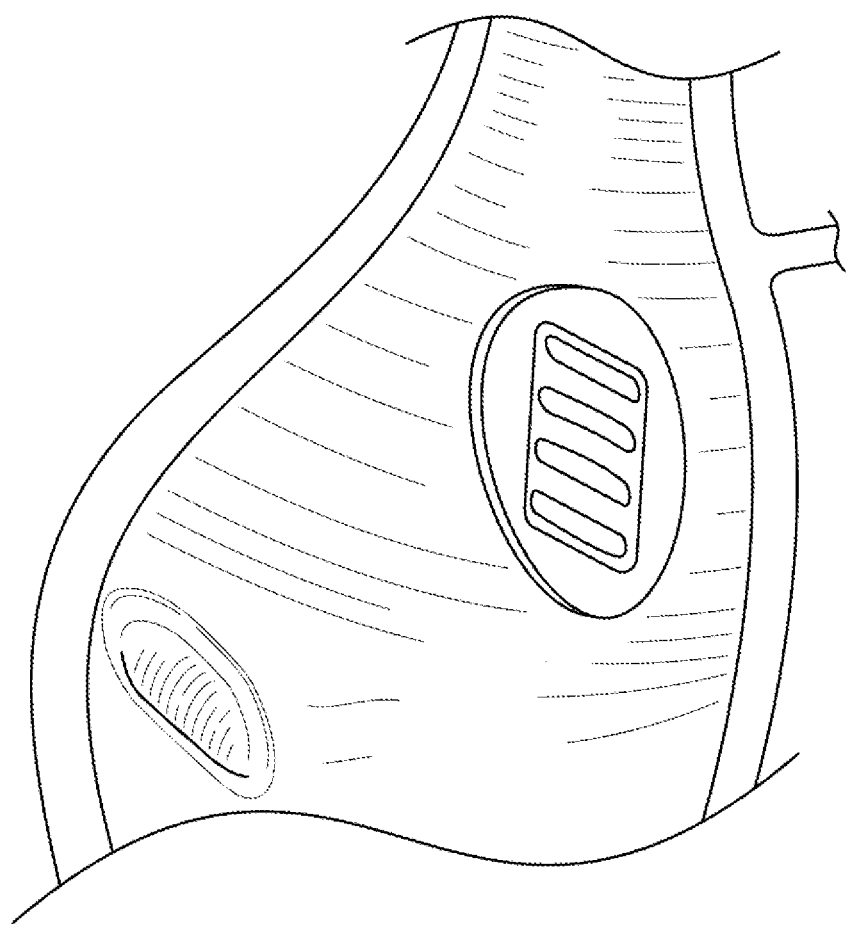
FIG. 3 depicts the foramen ovale following treatment.

FIG. 3 depicts the foramen ovale following treatment. The ridges 8 are areas where the tissue has been treated, and as a result, has melded together.

Figure 4:
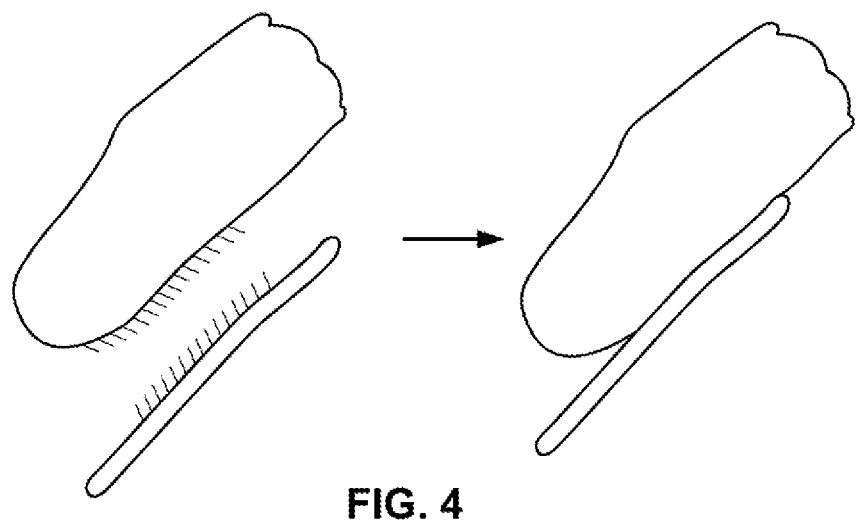
FIG. 4 depicts the molecular structural changes that occur with the treatment described herein.

FIG. 4 shows an example of the molecular structural changes that occur with the treatment described herein.

Figure 5:
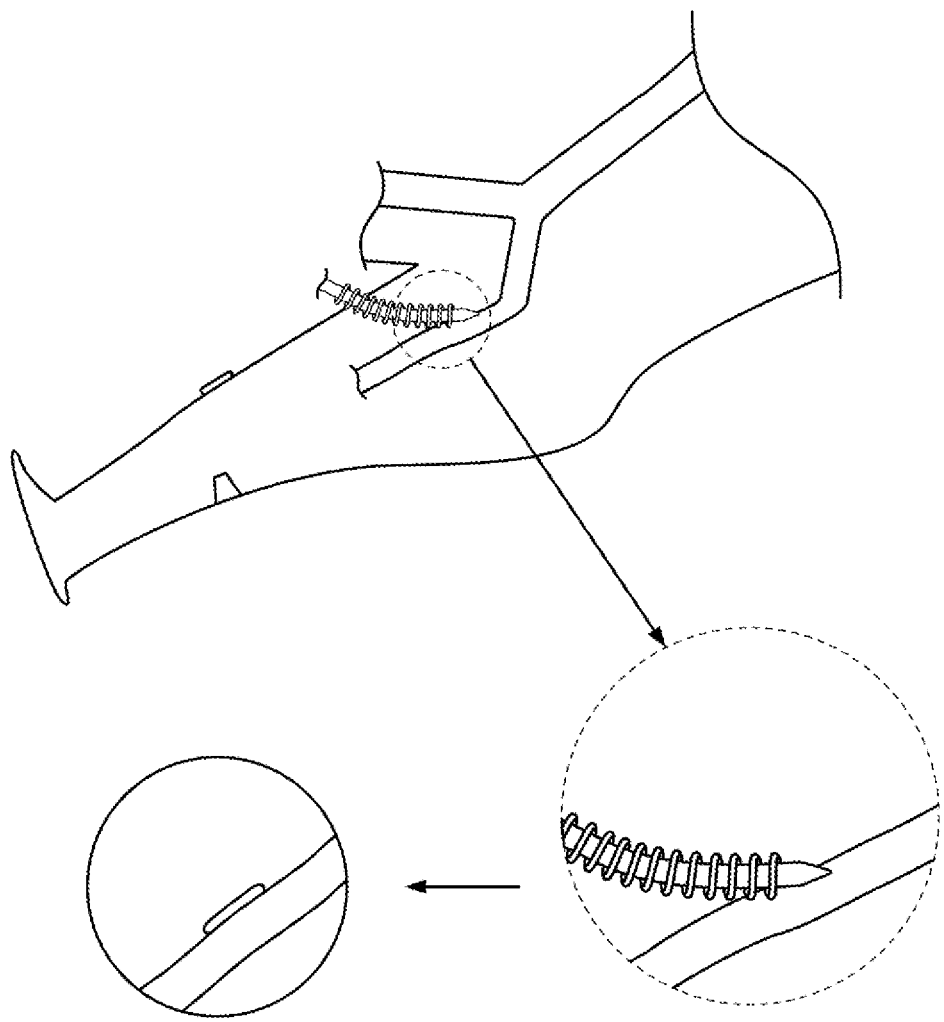
FIG. 5 depicts the use of the device for access puncture site closure.

FIG. 5 depicts the use of the device for access puncture site closure. In the illustrated example, the device or catheter is inserted through leg. It is noted that the principles of the invention may be applied at any access site, not just those limited as shown.

Figure 6A:
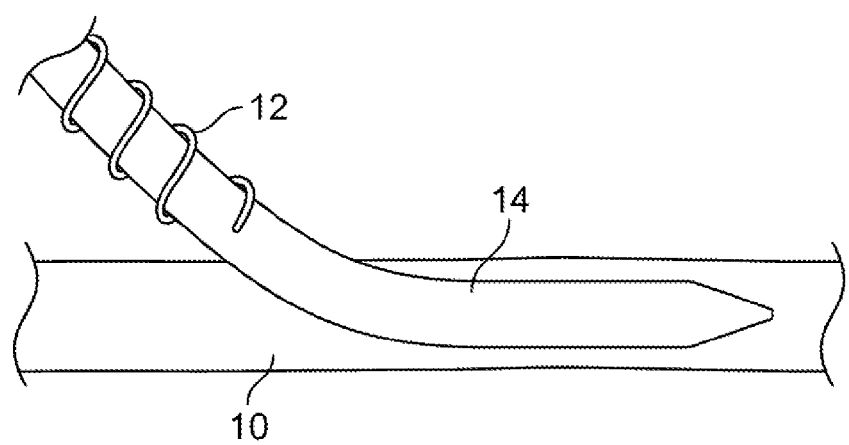
FIG. 6a-6c depicts a variation of the device closing a puncture site.
Figure 6B:
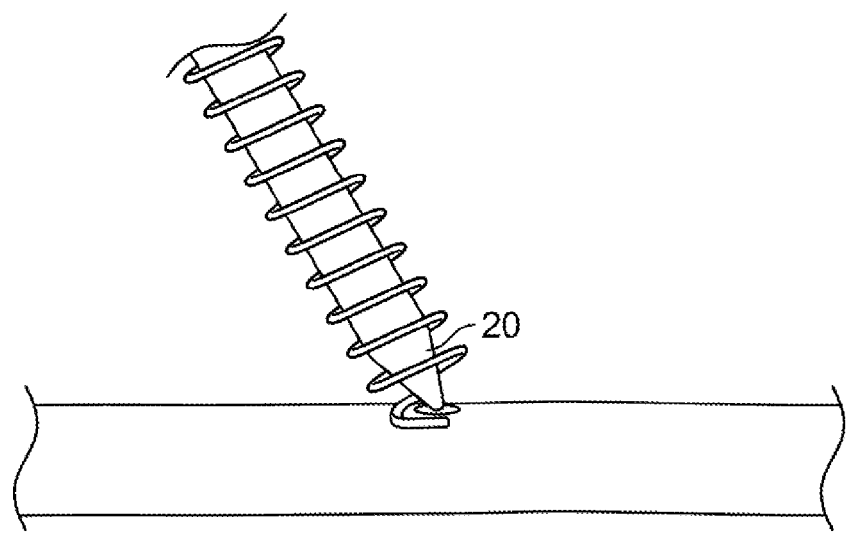

FIG. 6*a* illustrates the catheter 14 inserted into a vessel 10. The helical member 12 may be placed on the catheter during insertion, or may be threaded onto the catheter after the catheter is inserted into the vessel. In any case, the helical member 12 advances to the vessel 10. As shown in FIGS. 6A and 6B, upon approaching the vessel 10, the medical practitioner rotates the helical member 12 such that it penetrates the walls of the vessel 10. It is noted that the tip of the helical member 12 should not extend excessively into the vessel 10. Accordingly, determination of the location of the tip of the helical member 12 may be desirable. The tip may communicate with the catheter 14, or a portion thereof, by e.g., closing a circuit. Alternatively, the end of the helical member can act as an electrode capable of measuring capacitance, resistance or blood flow. When the tip enters the vessel, a lower resistance and capacitance as well as flow can be measured, providing confirmation of the proper placement of the helical member through the vessel wall. In such a case, when advancing the helical member 12 over the curved portion of the catheter 14, the tip of the helical member will separate from the catheter and, upon further rotation, engage the surface of the catheter. Therefore, a conductive surface on a portion of the catheter may assist in locating the tip of the helical member. Additional variations also exist, (e.g., having a tranducer that is equipped to determine Doppler effect caused by flowing blood, a sensor that determines the temperature difference when placed in flowing blood, a flow detector, etc.)

Figure 6C:
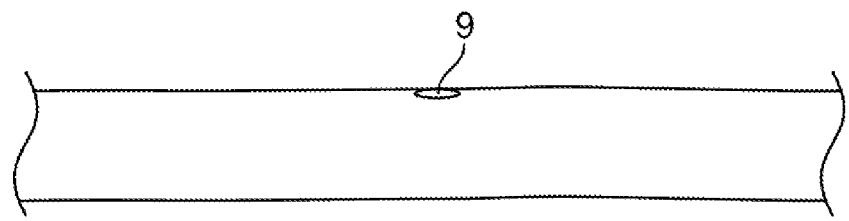

Next, as illustrated in FIG. 6*b* the catheter 10 is withdrawn and the coils of the helical member 12 compresses the tissue to assist in tissue closure. As noted above, the compression may be performed without any additional device (e.g., a shape memory alloy or compression of the helical turns of the member 12. Alternatively, or in combination, an obturator type device 20 may be located within the helical member 12 (the obturator may have been within the catheter and remains at the site, or it may be advanced after the catheter is withdrawn). The obturator compresses the tissue against the turns of the coil. Energy is then applied to the coil to cause minimal trauma to effect a healing response to generate collagen for plugging of the access site. As illustrated in FIG. 6*c*, after sufficient time passes, the obturator and coil are withdrawn from the site leaving the collagen plug to prevent bleeding.

Figure 7A:
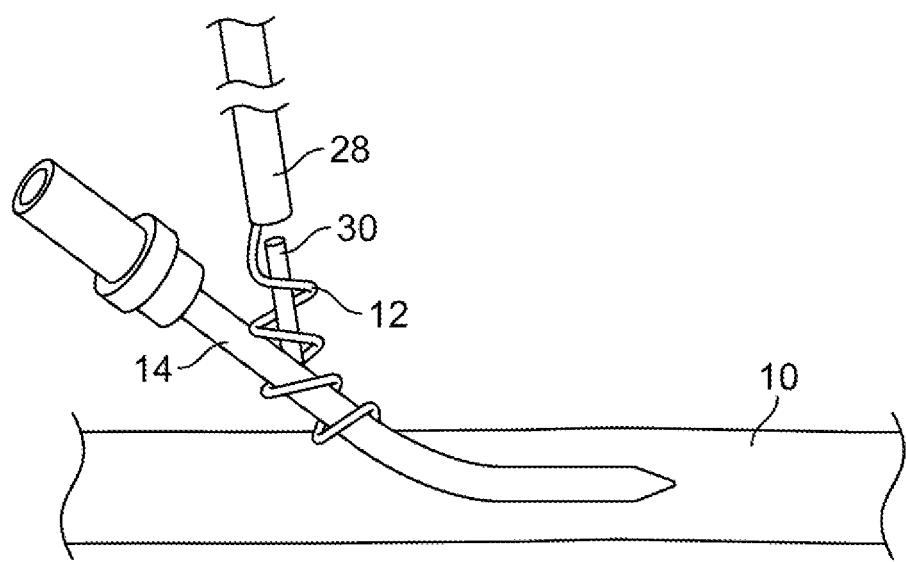
FIGS. 7a-7c depicts a variation of a device according to the present invention for attachment to a catheter where the device loads a helical member onto a catheter located within the body.
Figure 7B:
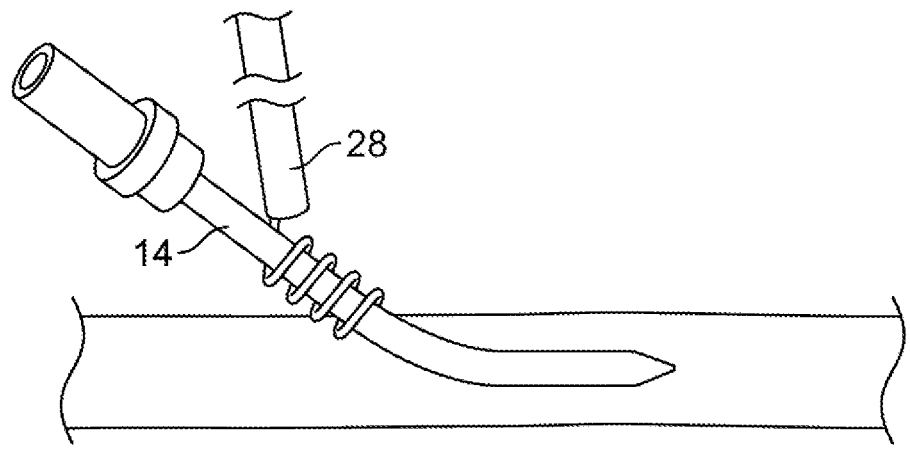
Figure 7C:
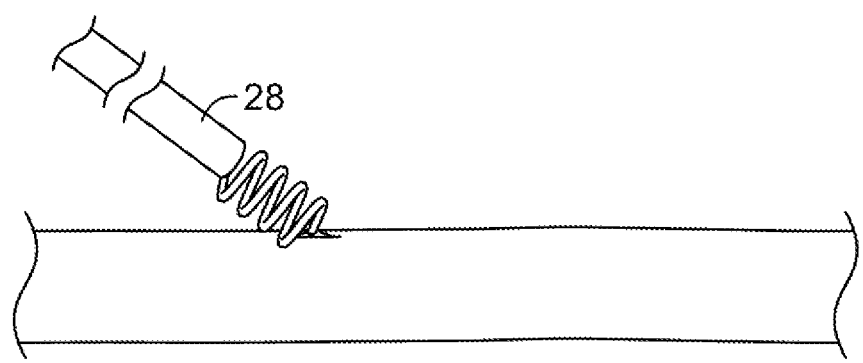

FIGS. 7*a*-7*c* depict a variation of a loading device 30 according to the present invention. The loading device allows for advancement or loading of a helical member onto a catheter. In this variation, the device loads a helical member 12 onto a catheter located within the patient. However, variations of the loading member may be configured to load the coil onto a catheter prior to insertion into a patient. As shown, the loading tool 30 comprises a loading portion and a catheter attachment portion. The catheter attachment portion may have a split so that it can be secured to the catheter subsequent to insertion of the catheter 14 into the patient. FIG. 7*a* illustrates the helical member 12 with handle 28 as the helical member 12 is loaded onto the loading tool 30. Once a desired length of the helical member 12 advances onto the catheter 14, the loading tool 30 may be removed. Alternatively, the loading tool 30 may be configured to remain on the catheter 14. In such a case, to enable loading of the helical member 12 onto the catheter, the helical member will be configured to be able to rotate independently of the loading tool 30. FIG. 7C illustrates removal of the catheter 14 from the patient.

Figure 8:
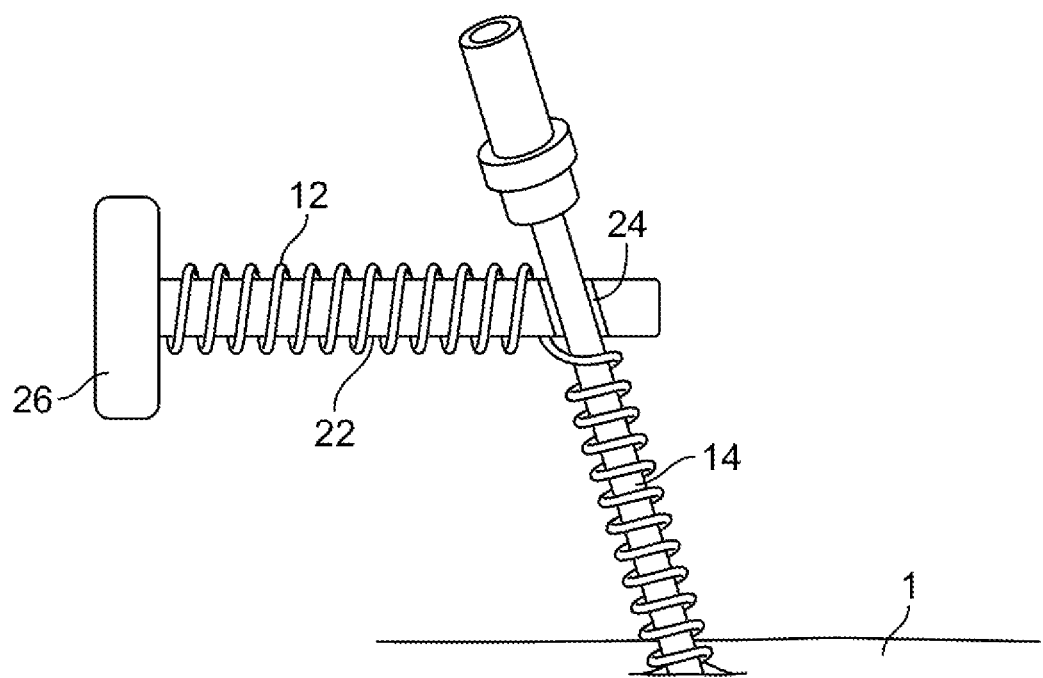
FIG. 8 depicts a variation of a device according to the present invention where the device loads a helical member onto a catheter located within the body.

FIG. 8 illustrates another variation of the invention of the present invention. As shown, to incorporate the operation of the invention with most types of catheters, a helical member 12 may be loaded upon a delivery member 22. The helical member 12 will reside either on or in the delivery member 22 such that, when needed, the delivery member may be coupled to a catheter 14 via a catheter slot or channel 24. The slot or channel 24 may be sized for the particular catheter (e.g., to match the gauge or French size of the catheter tubing.) Alternatively, the slot or channel 24 may be tapered to or otherwise accommodate a range of catheter tubing sizes. In one variation, the slot or channel 24 may have a locking mechanism (e.g., sized to press fit with the catheter, or a moveable flap, etc.) to allow the delivery member 22 to temporarily lock onto the catheter. The delivery member 22 may also have a handle portion 26 to allow for ease of manipulation by the medical practitioner. In some variations of the device, the handle may also be rotatable with respect to the catheter where the rotation drives the helical member 12 distally on the catheter. In another variation of the device, the delivery member 22 may contain a power supply to energize the helical member 12 to effectuate treatment.

It is noted that variations of the invention include combining features of the device described above. For example, the guide wire, helical member, and/or obturator may be incorporated into one or more devices. Moreover, the helical member may use any type of energy to heat the tissue (e.g., radiofrequency, resistive, laser, chemical, etc.)

Moreover, while the invention described herein may effect tissue closure using compression and heat, additives may also be incorporated. For example, the invention may also include the use of antibiotics, anti-inflammatories, anti-proliferatives, pain-killing medicines, heat-activated sealants/adhesives, polyethylene glycol, marking dyes, and/or other such medicines or additives.

While this description is intended to convey to anyone practiced in the art a device and method for closing a PFO, it is not limited to this specific embodiment, as a person so skilled in the art may modify the device and/or method while still remaining within the scope of this invention.

We claim:

1. A method for closing an access point in a blood vessel comprising:
    advancing a helical member over a catheter inserted into the blood vessel;
    advancing at least a portion of the helical member into a wall of the blood surrounding the access point;
    compressing the blood vessel wall against the helical member;
    applying energy to the blood vessel wall to generate a wound healing response sufficient to cause collagen production; and
    maintaining pressure during applying energy to close the access point.

2. The method of claim 1, where the collagen production is of a sufficient amount to cover the access point.

3. The method of claim 1, where the collagen production is of a sufficient amount to weld together unconnected tissue forming the access point.

4. The method of claim 1, wherein applying energy comprises applying an electrical current through the helical member.

5. The method of claim 1, wherein the catheter comprises an obturator.

6. The method of claim 1, wherein maintaining pressure during applying energy comprises compressing the blood vessel against a turn of the helical member.

\* \* \* \* \*